(12) United States Patent
Govari et al.

(10) Patent No.: US 9,474,850 B2
(45) Date of Patent: Oct. 25, 2016

(54) LASSO CATHETER WITH GUIDE WIRE

(71) Applicant: BIOSENSE WEBSTER (ISRAEL), LTD., Yokneam (IL)

(72) Inventors: Assaf Govari, Haifa (IL); Ariel Garcia, Glendora, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 819 days.

(21) Appl. No.: 13/710,874

(22) Filed: Dec. 11, 2012

(65) Prior Publication Data

US 2014/0163480 A1 Jun. 12, 2014

(51) Int. Cl.
*A61M 3/02* (2006.01)
*A61B 18/14* (2006.01)

(52) U.S. Cl.
CPC ........ *A61M 3/0279* (2013.01); *A61B 18/1492* (2013.01)

(58) Field of Classification Search
CPC .................. A61B 18/1492; A61M 3/0279
See application file for complete search history.

(56) References Cited

U.S. PATENT DOCUMENTS

| | | | |
|---|---|---|---|
| 6,254,598 B1 * | 7/2001 | Edwards | A61B 18/1206 606/41 |
| 2002/0151889 A1 | 10/2002 | Swanson et al. | |
| 2005/0033135 A1 | 2/2005 | Govari | |
| 2008/0281312 A1 | 11/2008 | Werneth et al. | |
| 2010/0168548 A1 | 7/2010 | Govari et al. | |
| 2011/0160719 A1 | 6/2011 | Govari et al. | |

* cited by examiner

*Primary Examiner* — Amanda Patton
(74) *Attorney, Agent, or Firm* — Wayne C. Jaeschke, Jr.

(57) ABSTRACT

Medical apparatus includes a flexible insertion shaft, which is adapted for insertion into a body of a patient. A resilient end section is fixed to the distal end of the insertion shaft and is formed so as to assume, when unconstrained, an arcuate shape. One or more electrodes are disposed at respective locations along the end section. A first lumen runs from the insertion shaft through the end section so as to convey an irrigation fluid to exit the end section through perforations of the electrodes. A second lumen runs through the insertion shaft to a distal opening and is configured to permit a guide wire to pass through the second lumen from the proximal end of the insertion shaft to exit distally through the distal opening, while conveying the irrigation fluid from the proximal end through the distal opening together with the guide wire.

2 Claims, 5 Drawing Sheets

LASSO CATHETER WITH GUIDE WIRE

FIELD OF THE INVENTION

The present invention relates generally to methods and devices for invasive medical treatment, and specifically to catheters.

BACKGROUND

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue.

Recently, circumferential ablation of the ostia of the pulmonary veins has gained acceptance as a treatment for atrial arrhythmias, and particularly for atrial fibrillation. For example, U.S. Patent Application Publication 2005/0033135, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section comprises one or more sensing electrodes, and its proximal end is joined at a fixed or generally known angle to a base section of the catheter. The catheter is inserted into the heart, and the curved section is positioned in contact with the wall of the PV, while the base section remains within the left atrium, typically positioned such that the joint with the curved section is at the ostium of the vein. The sensing electrodes may additionally perform ablation of selected sites, or the catheter may further comprise ablation elements.

U.S. Patent Application Publication 2010/0168548, whose disclosure is incorporated herein by reference, describes a lasso catheter for use in a system for electrical mapping of the heart. The catheter has an array of raised, perforated electrodes, which are in fluid communication with an irrigating lumen. There are position sensors on a distal loop section and on a proximal base section of the catheter. The electrodes are sensing electrodes that may be adapted for pacing or ablation. The raised electrodes securely contact cardiac tissue, forming electrical connections having little resistance.

U.S. Patent Application Publication 2008/0281312 describes an ablation therapy system and systematic method for treating continuous atrial fibrillation. A carrier assembly and flexible outer catheter tube are percutaneously advanced over a guide wire whose distal end has been inserted into a pulmonary vein of the patient. After proper deployment of the carrier assembly, and after proper orientation and location of the electrodes relative to the targeted PV tissue, the carrier assembly is advanced distally, as a unit, along the guide wire to contact with the ostial tissue surrounding the Left Superior Pulmonary Vein (LSPV). Once sufficient tissue contact has been established, and the mapping procedure has confirmed the presence of aberrant conductive pathways, ablation energy may be passed through the output electrodes.

SUMMARY

Embodiments of the present invention that are described hereinbelow provide invasive devices and methods for contacting tissue within the body with enhanced ease of use and therapeutic results.

There is therefore provided, in accordance with an embodiment of the invention, medical apparatus, which includes a flexible insertion shaft, having a proximal end and a distal end, which is adapted for insertion into a body of a patient. A resilient end section is fixed to the distal end of the insertion shaft and is formed so as to assume, when unconstrained, an arcuate shape. One or more electrodes are disposed at respective locations along the end section and have perforations therein. A first lumen runs from the insertion shaft through the end section so as to convey an irrigation fluid from the proximal end of the insertion shaft to exit the end section through the perforations of the electrodes. A second lumen runs through the insertion shaft to a distal opening at the distal end of the insertion shaft, and is configured to permit a guide wire to pass through the second lumen from the proximal end of the insertion shaft to exit distally through the distal opening, while conveying the irrigation fluid from the proximal end through the distal opening together with the guide wire.

In some embodiments, the guide wire is configured for insertion through a vascular system of a patient into a target vessel, and the insertion shaft is configured to be advanced distally, after the insertion of the guide wire into the target vessel, over the guide wire toward the target vessel. Typically, the resilient end section is configured, when the insertion shaft has been advanced to within a proximity of the target vessel, to contact tissue in the body along an arc surrounding the target vessel. In one embodiment, the target vessel is a pulmonary vein, and the guide wire is configured for insertion through a left atrium of a heart of the patient into the pulmonary vein, and the resilient end section is configured to contact and apply electrical energy to myocardial tissue surrounding the pulmonary vein via the one or more electrodes so as to ablate the tissue. Optionally, a distal tip of the resilient end section may be configured for attachment to the guide wire while the insertion tube is being advanced distally over the guide wire.

In a disclosed embodiment, the apparatus includes a manifold, which is coupled to supply the irrigation fluid from a single fluid source to both of the first and second lumens and may be configured to inhibit a flow of the irrigation fluid through the second lumen in response to back-pressure from the first lumen.

There is also provided, in accordance with an embodiment of the invention, medical apparatus, which includes a flexible insertion shaft, having a proximal end and a distal end, which is adapted for insertion into a body of a patient. First and second lumens run through the insertion shaft so as to convey an irrigation fluid from the proximal end of the insertion shaft to respective first and second outlets in a vicinity of the distal end. A manifold is coupled to supply the irrigation fluid from a single fluid source to both of the first and second lumens while inhibiting a flow of the irrigation fluid through the second lumen in response to back-pressure from the first lumen.

In a disclosed embodiment, the manifold includes a flexible diaphragm, which is coupled to an actuator and is configured to deform in response to the back-pressure so as to cause the actuator to close a valve on the second lumen. Typically, the manifold has a single inlet for receiving the irrigation fluid from an irrigation pump and first and second outlets, separated by the diaphragm, for supplying the irrigation fluid to the first and second lumens, respectively.

In some embodiments, the apparatus includes one or more electrodes, which are coupled to the distal end of the insertion shaft and are configured to be brought into contact with and to apply electrical energy to tissue in the body so as to ablate the tissue, wherein at least the first outlets include perforations in the electrodes.

There is additionally provided, in accordance with an embodiment of the invention, a method for treatment, which includes providing a medical probe including a flexible insertion shaft having a resilient end section at the distal end of the insertion shaft and containing at least first and second lumens. A guide wire is inserted into a body of a patient so as to reach a target location in the body. The medical probe is advanced over the guide wire to the target location while passing the guide wire through the second lumen, wherein the guide wire exits the second lumen through a distal opening of the second lumen at the distal end of the insertion shaft, so as to bring the end section of the medical probe into contact with tissue in the body along an arc at the target location. One or more electrodes at respective locations on the end section are actuated to apply electrical energy to the tissue along the arc. While actuating the one or more electrodes, irrigation fluid is conveyed through the first lumen via perforations in the electrodes to the tissue and through the second lumen to exit the distal opening together with the guide wire.

The present invention will be more fully understood from the following detailed description of the embodiments thereof, taken together with the drawings in which:

DETAILED DESCRIPTION OF EMBODIMENTS

Cardiologists often find it difficult to position and align a lasso catheter precisely around the pulmonary veins. Embodiments of the present invention address this problem by means of a guide wire, which is inserted into the pulmonary vein ahead of the catheter.

In the disclosed embodiments, a medical probe, such as a lasso catheter, contains a lumen (also referred to as a channel) in the catheter shaft, through which the guide wire may pass. In typical operation, a sheath is inserted through the vascular system and into the left atrium through the interatrial septum. The guide wire is then inserted through the sheath to a target location, typically into a target vessel, such as one of the pulmonary veins. Finally, the lasso catheter (with the lasso straightened by the sheath) is inserted through the sheath and advanced over the guide wire. Once the lasso passes out of the sheath into the left atrium, it resumes its arcuate form. As the operator continues to push the catheter forward, the guide wire guides the shaft toward the pulmonary vein until the lasso seats against the ostium of the vein and contacts the tissue along an arc.

It is desirable that the channel through which the guide wire passes be irrigated with positive pressure of irrigation fluid, in order to prevent formation or blood clots in the area of the wire outlet at the distal end of the shaft. The electrodes on the end section of the catheter may also be irrigated, so as to deliver irrigation fluid through perforations in the electrodes to the tissue during ablation. In an embodiment that is described hereinbelow, the catheter contains two irrigation lumens, one of which serves as the channel for the guide wire, and the other of which delivers the irrigation fluid to the electrodes. A manifold in the catheter delivers irrigation fluid from a single source, such as an irrigation pump, to both lumens, while controlling fluid pressure in order to inhibit excessive flow in one of the lumens in the event that the outlet of the other lumen is blocked.

A guide wire and modified lasso catheter of this sort may be used not only in ablating around the pulmonary veins, but also in other diagnostic and therapeutic applications of medical probes having specially-shaped distal ends. The manifold may similarly be used to control flow and pressure in other applications in which an irrigation fluid is conveyed simultaneously through multiple lumens in an invasive medical probe.

Figure 1:
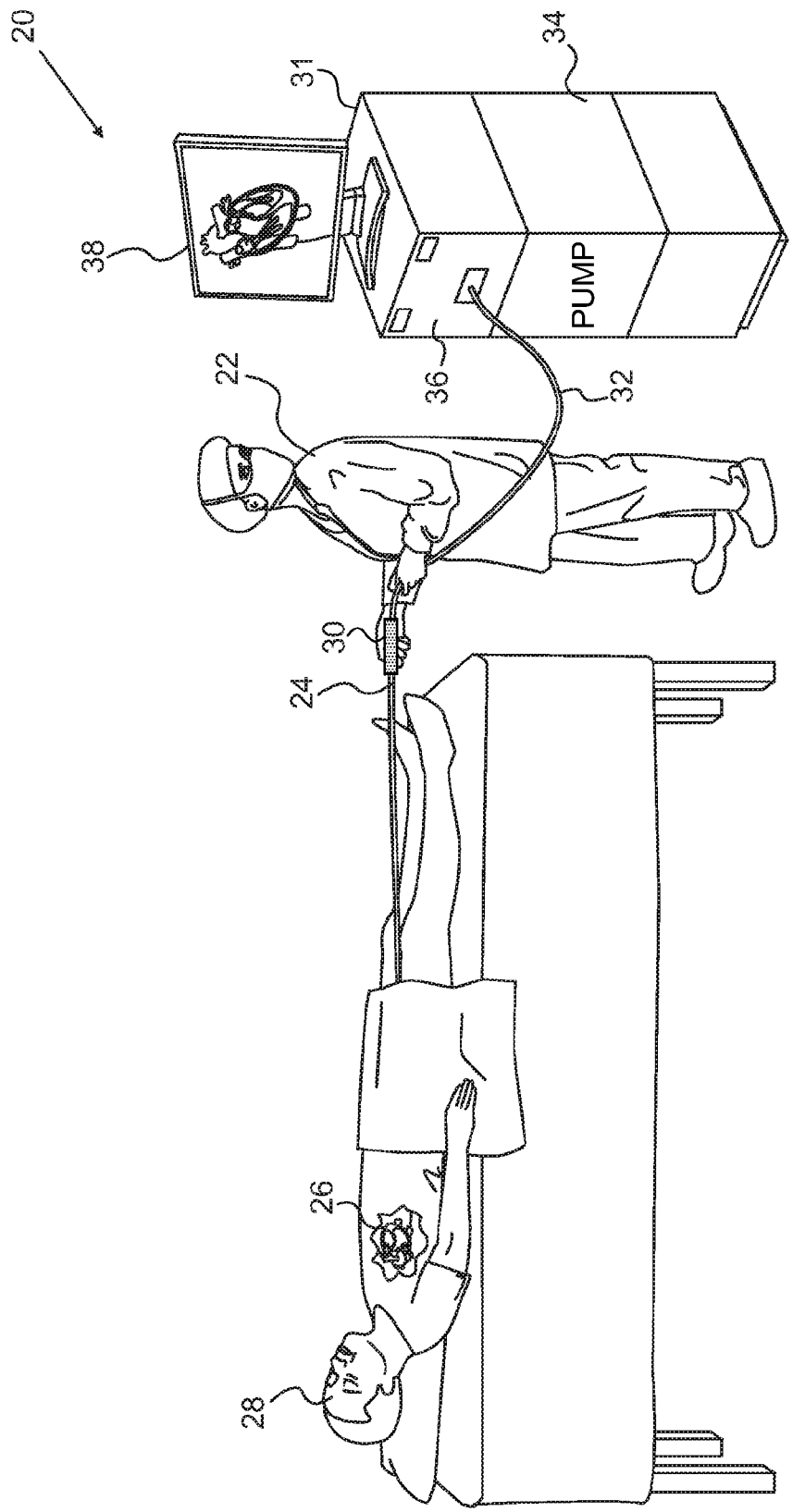
FIG. 1 is a schematic, pictorial illustration of a system for ablation of tissue in the heart, in accordance with an embodiment of the present invention.

FIG. 1 is a schematic pictorial illustration of a system 20 for ablation of tissue in a heart 26 of a patient 28, in accordance with an embodiment of the present invention. An operator 22, such as a cardiologist, inserts a flexible probe, such as a catheter 24, through the vascular system of patient 28 so that the distal end of the catheter enters a chamber of the patient's heart. Operator 22 advances the catheter so that the end section of the catheter engages endocardial tissue at a target location or locations, as shown in the figures that follow. The operator typically uses a handle 30 to manipulate and control the motion of the catheter inside the patient's body.

Catheter 24 is connected by a suitable cable 32 to a console 31. The console comprises an RF generator 36 for applying RF energy through electrodes on the end section of the catheter in order to ablate the tissue contacted by the distal section. In addition, an irrigation pump 34 supplies an irrigation fluid, such as saline solution, to irrigate the distal end of catheter 24, as described further hereinbelow. Alternatively or additionally, catheter 24 may be used for other diagnostic and/or therapeutic functions, such as intracardiac electrical mapping or other types of ablation therapy, and similar sorts of probes may be used for diagnostic and therapeutic functions in organs other than the heart.

System 20 may use position sensing to track the end section of catheter 24 inside heart 26. For example, the system may use magnetic position sensing to find position coordinates of the end section of the catheter, as described, for example, in the above-mentioned U.S. Patent Application Publication 2005/0033135 or in U.S. Patent Application Publication 2011/0160719, whose disclosure is incorporated herein by reference. This sort of position sensing is implemented in the CARTO™ system produced by Biosense Webster Inc. (Diamond Bar, Calif.). Alternatively or additionally, system 20 may use other position-sensing techniques that are known in the art, such as impedance-based or ultrasonic position sensing.

Figure 2:
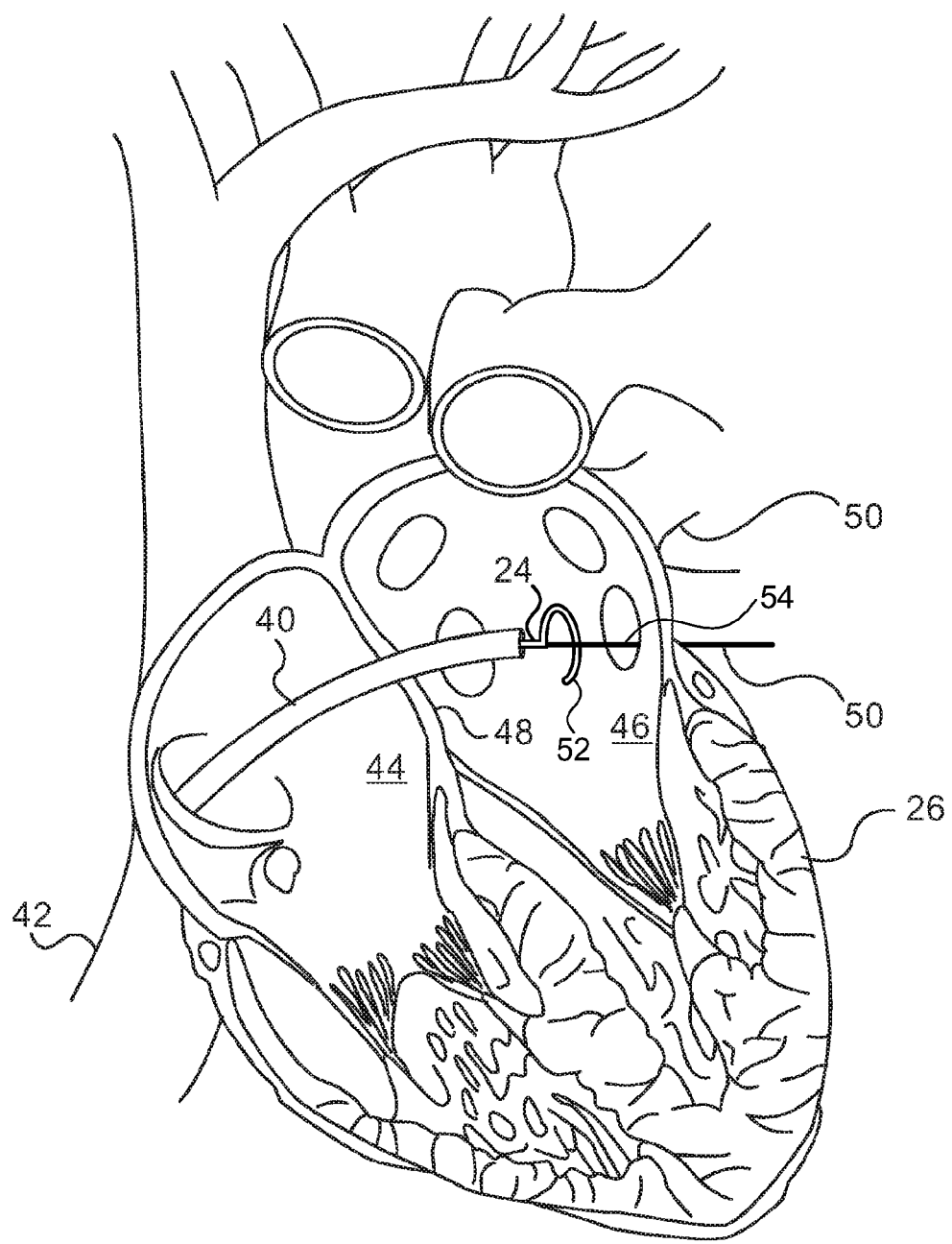
FIG. 2 is a schematic sectional view of a heart showing insertion of a catheter into the left atrium, in accordance with an embodiment of the present invention.

FIG. 2 is a schematic sectional view of heart 26, showing insertion of catheter 24 into the heart, in accordance with an embodiment of the present invention. To insert the catheter in the pictured embodiment, operator 22 first passes a sheath 40 percutaneously through the vascular system and into right atrium 44 of the heart through ascending vena cava 42. The sheath penetrates through interatrial septum 48, typically via the fossa ovalis, into left atrium 46. Alternatively, other approach paths may be used. A guide wire 54 is then threaded through sheath 40 and into one of pulmonary veins 50. Operator 22 may align sheath 40 and guide wire 54 inside left atrium 46 with the axis of pulmonary vein 50 using the position sensing methods described above, for example, along with a pre-acquired map or image of heart 26. Alternatively or additionally, the alignment may be performed under fluoroscopic or other means of visualization.

Catheter 24 is then advanced over wire 54 through the lumen of sheath 40 until an end section 52 of the catheter passes out of the distal opening at the end of the sheath into left atrium 46, as shown in FIG. 2. The end section is resilient and is formed so as to define an arc when unconstrained, as is shown and described in greater detail hereinbelow with reference to FIG. 3. While end section 52 is passing through sheath 40, however, the smaller inner diameter of the sheath holds the end section straight and roughly parallel to the catheter axis.

Figure 3:
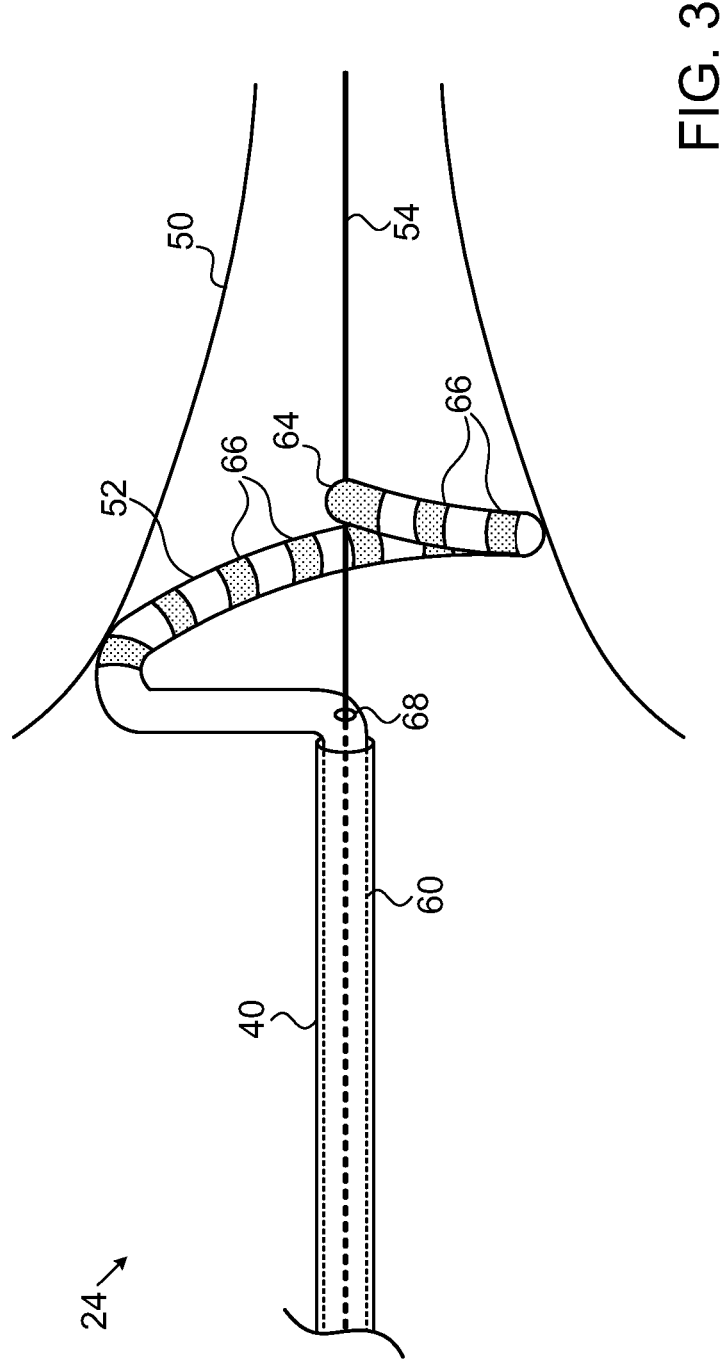
FIG. 3 is a schematic, pictorial illustration showing engagement of ostial tissue by the end section of a catheter, in accordance with an embodiment of the present invention.

FIG. 3 is a schematic, pictorial illustration showing engagement of ostial tissue by end section 52 of catheter 24, in accordance with an embodiment of the present invention. End section 52 is connected at its base to the distal end of a flexible insertion shaft 60 of the catheter. Shaft 60 and end section 52 typically comprise an outer shell made from a suitable flexible biocompatible material, such as polyurethane, having a diameter around 2-3 mm, with internal lumens as described below and internal wiring (not shown) as required. In one embodiment, in which the catheter is designed for therapeutic ablation, the size of the shaft is 7 Fr (about 2.3 mm diameter), while the end section is of the same or slightly larger size (such as 7.5 Fr). In other embodiments, for diagnostic measurements, the shaft is 7 Fr, while the end section may have a diameter between 1 and 2.5 mm.

End section 52 is formed as a complete or partial lasso, i.e., as a preformed arcuate structure, which typically subtends between 180° and 360°. The radius of curvature of end section 52, when unconstrained, is typically between 7.5 mm and 15 mm. Because the arc structure is resilient and, possibly, slightly helical, when end section 52 is positioned in the heart (against the ostium of pulmonary vein 50, for example), and insertion shaft 60 is advanced distally over wire 54, the end section will press against the heart tissue over the entire length of the arc, thus facilitating good tissue contact. The arcuate and possibly helical shape of end section 52 may be maintained, for example, by incorporating a thin strut made from a shape memory material, such as Nitinol (not shown in the figures), in the desired shape within the end section. The strut is made sufficiently flexible to permit the end section to straighten during insertion and withdrawal through sheath 40, but to resume its arcuate form when it is unconstrained inside the heart chamber.

End section 52 comprises an array of electrodes coupled along its length, including, in this example, a tip electrode 64 extending over the distal tip of the end section and proximal electrodes 66 distributed along the end section. Typically, electrodes 66 have a width between 1 mm and 4 mm, and are spaced between 1 mm and 10 mm apart. Electrodes 64 and 66 are connected to the proximal end of catheter 24 by wires (not shown) running through the catheter. Alternatively, other electrode configurations may be used. For example, the end section may include smaller "bump" electrodes, as described in the above-mentioned U.S. Patent Application Publication 2010/0168548. In any of these configurations, the electrodes may be used for sensing and/or ablation. In order to ablate an entire annulus around a pulmonary vein, for example, catheter 24 may be rotated ("clocked") about its axis while actuating the electrodes to apply RF electrical energy to the tissue, as noted above.

Guide wire 54 passes through a lumen (shown in FIGS. 4A and 4B) in shaft 60 and exits the shaft through a distal opening 68 of the lumen. After inserting the guide wire into pulmonary vein 50, as shown in FIG. 3, the operator advances shaft 60 over the wire until end section 52 reaches the ostium of the target pulmonary vein 50. Optionally, the distal tip of end section 52, in the vicinity of electrode 64, may be attached to wire 54, as well, to aid in directing the end section straight toward the axis of vein 50. This attachment may be temporary, so that the distal tip is released once it reaches the target location.

In this manner, operator 22 brings the arcuate end section 52 of catheter 24 into contact with the ostium of vein 50, so that the end section either partly or fully surrounds the vein (depending on the angle subtended by the arc), as shown in FIG. 3. Position sensors, such as magnetic transducers, in shaft 60 and/or in end section 52 (not shown in the figures) may provide position readings to assist the operator in positioning and manipulating catheter 24, as described, for example, in the above-mentioned U.S. Patent Application Publications 2005/0033135 and 2010/0168548. The operator then rotates the catheter about its axis within the sheath so that the end section traces an annular path around the circumference of the vein. Meanwhile, the operator actuates RF generator 36 to ablate the tissue along the path. After completing this procedure around one pulmonary vein, the operator may shift the sheath and catheter and repeat the procedure around one or more of the other pulmonary veins.

To provide local cooling and prevent adhesion during ablation, one or more of electrodes 64 and 66 may have perforations to serve as outlets for irrigation. Any suitable sort of perforations may be formed in the electrodes, such as those described and shown, for example, in U.S. Patent Application Publication 2010/0168548. The perforations are coupled to one or more lumens in end section 52, which carry irrigation fluid from shaft 60 to the electrodes and to the tissue surrounding them. In addition, it is desirable that the lumen through which guide wire 54 passes in shaft 60 be irrigated as well, to prevent formation of blood clots in the vicinity of opening 68. Details of an arrangement of irrigation lumens that may be used for this purpose are described hereinbelow and are shown in the figures that follow.

Figure 4A:
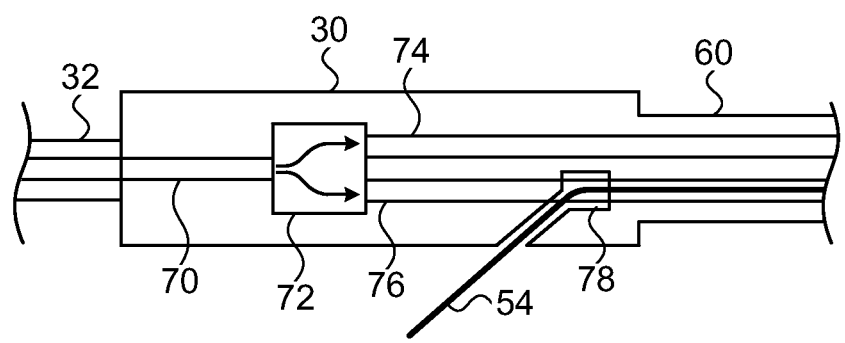
FIG. 4A is a schematic internal view of a catheter handle, showing an irrigation manifold therein, in accordance with an embodiment of the present invention.
Figure 4B:
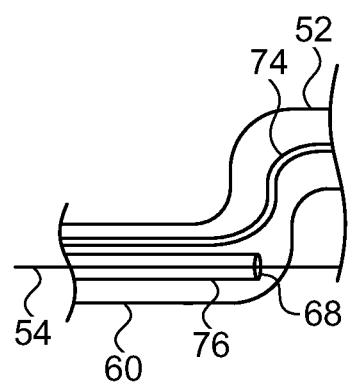
FIG. 4B is a schematic detail view of a part of a distal section of a catheter, showing lumens within the catheter, in accordance with an embodiment of the present invention.

FIGS. 4A and 4B are schematic detail views showing lumens 74 and 76 inside catheter 24, in accordance with an embodiment of the present invention. FIG. 4A shows the proximal end of the catheter, in the vicinity of handle 30, while FIG. 4B shows the distal end, at the base of end section 52. Lumen 74 conveys irrigation fluid to electrodes 64 and 66, while lumen 76 serves as the channel for passage of guide wire 54 through shaft to distal opening 68. At the proximal end of shaft 60, the guide wire is threaded out through a port 78, which may be located, for example, in handle 30 as shown in FIG. 4A. Port 78 typically has a seal to prevent leakage of irrigation fluid from the handle. Optionally, shaft 60 may contain one or more additional lumens (not shown), such as a dedicated lumen for irrigating tip electrode 64 separately from proximal electrodes 66.

Irrigation fluid is supplied to lumens 74 and 76 by pump 34 via a feed tube 70 passing through cable 32. To avoid the need for two pumps or for a pump with a specialized dual outlet, an irrigation manifold 72 in catheter 24 divides the fluid provided at the manifold inlet by the single feed tube 70 between outlets to lumens 74 and 76. Manifold 72 may conveniently be located in handle 30, as shown in FIG. 4A. Alternatively, a manifold of this sort may be deployed at any suitable location along insertion shaft 60, including at the distal end of the insertion shaft, or possibly may be integrated into cable 32.

Figure 5:
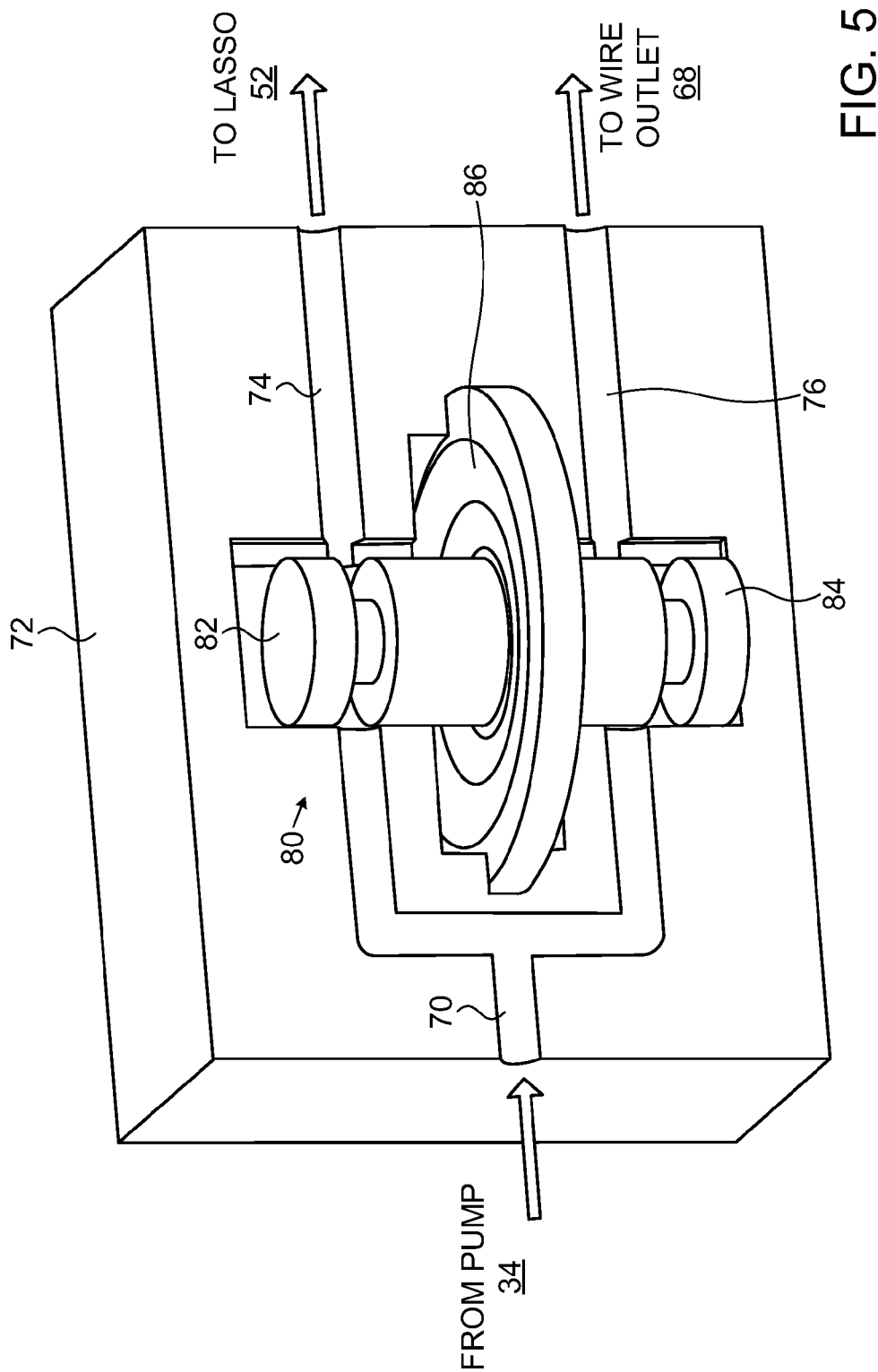
FIG. 5 is a schematic, cutaway view of an irrigation manifold, in accordance with an embodiment of the present invention.

FIG. 5 is a schematic, cutaway view of irrigation manifold 72, in accordance with an embodiment of the present invention. Manifold 72 contains a pressure regulator 80, whose function is to automatically distribute fluid from pump 34 between lumens 74 and 76 so as to ensure that the flow rate through both lumens is maintained within desired limits notwithstanding possible blockages of the fluid outlets at the distal end of catheter 24. Such blockages may occur, for example, when electrodes 64 and/or 66 press against tissue in the heart, so that the tissue closes off at least some of the perforations in the electrodes through which the irrigation fluid would otherwise flow out. In such a case, in the absence of regulator 80, back-pressure in lumen 74 will propagate to lumen 76 and may cause excessive outflow of irrigation fluid through distal opening 68 along with reduced irrigation of the electrodes.

To inhibit flow through lumen 76 under such conditions, regulator 80 comprises a piston 82, which is coupled to a flexible diaphragm 86 located between the outlets of manifold 72 to lumens 74 and 76. A grooved actuator 84 at the end of piston 82 adjacent to lumen 76 defines a valve, which is opened and shut by the movement of the piston (vertical movement in the view shown in the figure). Excess back-pressure from lumen 74 will distort diaphragm 86 in the downward direction, causing piston 82 to move downward with the diaphragm and thus close the valve on lumen 86, as shown in the figure. In other words, increased fluid pressure in lumen 74 will automatically give rise to inhibit fluid flow, due to motion of piston 82, in the path to lumen 76. Thus, the desired proportion of flow between lumens 74 and 76 is maintained notwithstanding changes in back-pressure.

Although regulator 80, as shown in FIG. 5, is advantageous in terms of compactness and simplicity, other fluid regulation mechanisms may alternatively be used to maintain the desired distribution of irrigation fluid between lumens 74 and 76. On the other hand, the principles of regulator 80 may similarly be applied in other sorts of medical devices in which fluid from a single source is to be distributed among multiple lumens. For example, an arrangement of this sort may be used to maintain a desired distribution of irrigation fluid among multiple electrodes at the distal end of a catheter, such as between electrodes 64 and 66.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Medical apparatus, comprising:
   a flexible insertion shaft, having a proximal end and a distal end, which is adapted for insertion into a body of a patient;
   a resilient end section, which is fixed to the distal end of the insertion shaft and is formed so as to assume, when unconstrained, an arcuate shape;
   one or more electrodes, which are disposed at respective locations along the end section and have perforations therein;
   a first lumen, which runs from the insertion shaft through the end section so as to convey an irrigation fluid from the proximal end of the insertion shaft to exit the end section through the perforations of the electrodes;
   a second lumen, which runs through the insertion shaft to a distal opening at the distal end of the insertion shaft, and is configured to permit a guide wire to pass through the second lumen from the proximal end of the insertion shaft to exit distally through the distal opening, while conveying the irrigation fluid from the proximal end through the distal opening together with the guide wire; and a manifold, which is coupled to supply the irrigation fluid from a single fluid source to both of the first and second lumens.

2. The apparatus according to claim 1, wherein the manifold is configured to inhibit a flow of the irrigation fluid through the second lumen in response to back-pressure from the first lumen.

* * * * *